United States Patent
Breuninger et al.

(10) Patent No.: US 10,610,097 B2
(45) Date of Patent: Apr. 7, 2020

(54) SYSTEM AND A METHOD FOR CORRECTIVE LENS DETERMINATION

(71) Applicants: Carl Zeiss Vision International GmbH, Aalen (DE); Carl Zeiss AG, Oberkochen (DE)

(72) Inventors: Tobias Breuninger, Riederich (DE); Frank Schäffel, Tübingen (DE); Siegfried Wahl, Donzdorf (DE); Karsten Lindig, Erfurt (DE); Arne Ohlendorf, Tübingen (DE); Jesús-Miguel Cabeza-Guillén, Aalen (DE)

(73) Assignees: Carl Zeiss Vision International GmbH, Aalen (DE); Carl Zeiss AG, Oberkochen (DE)

( * ) Notice: Subject to any disclaimer, the term of this patent is extended or adjusted under 35 U.S.C. 154(b) by 0 days.

(21) Appl. No.: 16/232,414

(22) Filed: Dec. 26, 2018

(65) Prior Publication Data
US 2019/0167093 A1  Jun. 6, 2019

Related U.S. Application Data

(63) Continuation of application No. PCT/EP2017/066335, filed on Jun. 30, 2017.

(30) Foreign Application Priority Data

Jun. 30, 2016 (DE) ........................ 10 2016 112 023

(51) Int. Cl.
*A61B 3/14* (2006.01)
*A61B 3/103* (2006.01)
(Continued)

(52) U.S. Cl.
CPC ............ *A61B 3/103* (2013.01); *A61B 3/0008* (2013.01); *A61B 3/10* (2013.01); *A61B 3/14* (2013.01);
(Continued)

(58) Field of Classification Search
CPC ... A61B 3/0008; A61B 3/10–15; A61B 3/103; A61B 3/152; G06T 7/74;
(Continued)

(56) References Cited

U.S. PATENT DOCUMENTS 3,775,012 A  11/1973  Ling et al.
4,848,899 A  7/1989  Kobayashi et al.
(Continued)

FOREIGN PATENT DOCUMENTS

CN  103653654 A  3/2014
CN  204260054 U  4/2015
(Continued)

OTHER PUBLICATIONS

H. Goersch, Wörterbuch der Optometrie, 2. Edition, Verlag Bode GmbH & Co. KG, Pforzheim, 2001, p. 26, and English-language translation thereof.
(Continued)

*Primary Examiner* — Mustak Choudhury
(74) *Attorney, Agent, or Firm* — Thrive IP®; Georg M. Hasselmann

(57) ABSTRACT

A component for a mobile computer device, such as a smartphone, can be secured to the housing of the mobile computer device. The component can deflect the light of a built-in light source of the mobile computer device with an optical element and optionally filter the same, or can provide its own light source to improve the option of measuring eccentric photorefraction using the mobile computer device.

8 Claims, 7 Drawing Sheets

(51) Int. Cl.
  *G02B 19/00* (2006.01)
  *A61B 3/10* (2006.01)
  *G06T 7/73* (2017.01)
  *A61B 3/00* (2006.01)
  *H04M 1/02* (2006.01)
  *G02B 13/00* (2006.01)

(52) U.S. Cl.
  CPC ..... *G02B 19/0019* (2013.01); *G02B 19/0061* (2013.01); *G02B 19/0066* (2013.01); *G06T 7/74* (2017.01); *H04M 1/0264* (2013.01); *G02B 13/001* (2013.01)

(58) Field of Classification Search
  CPC ............ G02B 19/0061; G02B 19/0066; G02B 19/0019; G02B 13/001; G02B 27/0093; G02B 27/0172; G02B 27/225; G03B 17/56; G03B 17/565; H04M 1/0264
  USPC ............... 351/206–208, 246; 345/8; 396/661
  See application file for complete search history.

(56) References Cited

U.S. PATENT DOCUMENTS

| | | | |
|---|---|---|---|
| 9,547,218 | B2 | 1/2017 | Takahashi et al. |
| 2003/0108350 | A1* | 6/2003 | Brauning ............... A61B 3/103 396/661 |
| 2013/0235346 | A1 | 9/2013 | Huang |
| 2015/0002817 | A1 | 1/2015 | Alasaarela et al. |
| 2016/0120402 | A1 | 5/2016 | Limon |
| 2016/0296111 | A1* | 10/2016 | Russo ..................... A61B 3/12 |
| 2017/0188813 | A1 | 7/2017 | Arnold et al. |

FOREIGN PATENT DOCUMENTS

| | | | |
|---|---|---|---|
| DE | 2232410 | A1 | 1/1973 |
| DE | 19719694 | A1 | 11/1998 |
| DE | 102007031923 | A1 | 7/2008 |
| DE | 102015100147 | A1 | 3/2016 |
| EP | 1308128 | A2 | 5/2003 |
| EP | 2924977 | A1 | 9/2015 |
| WO | 2015071779 | A1 | 5/2015 |
| WO | 2016022215 | A1 | 2/2016 |

OTHER PUBLICATIONS

H. Goersch, Wörterbuch der Optometrie, 2. Edition, Verlag Bode GmbH & Co. KG, Pforzheim, 2001, p. 239, and English-language translation thereof.

W. Wesermann et al. "Photorefraktion—Ein objektives Screening—Verfahren zur Refraktionsbestimmung [Photorefraction—An objective screening method for the determination of refraction]," DOZ—Deutsche Optiker Zeitung, Nov. 1992, pp. 50 to 54, 1992, and English-language translation thereof.

Schaeffel et al.: "Infrared photoretinoscope," Appl. Opt. 26, pp. 1505 to 1509, 1987.

Gekeler et al.: "Measurement of astigmatism by automated infrared photoretinoscopy," Optom. Vis. Sci. Jul. 1997, vol. 74(7), pp. 472 to 482.

Angi et al.: "Higher eccentricity of the LED source in photorefraction extends the range of measurement to high ametropias," ARVO Annual Meeting Abstract, Investigative Ophthalmology & Visual Science Apr. 2014, vol. 55, 435.

Stramare: "Screening for refractive errors in children using the 2WIN, binocular refractometer," ARVO Annual Meeting Abstract, Investigative Ophthalmology & Visual Science Apr. 2014, 2014, vol. 55, 4500.

Vaughan et al.: "Photoscreening for Refractive Error and Strabismus With a Smartphone App," ARVO Annual Meeting Abstract, Investigative Ophthalmology & Visual Science Apr. 2014, vol. 55, 436.

Roorda: "Eccentric photorefraction method," internet website, available at http://roorda.vision.berkeley.edu/photoref.htm, published to the world wide web on Mar. 21, 2016.

International Preliminary Examination Report and English-language translation thereof issued in PCT/EP2017/066335, to which this application claims priority, dated Nov. 27, 2018.

"Ophthalmic optics—Spectacle lenses—Vocabulary" (ISO 13666:2012); German and English version EN ISO 13666:2012, Oct. 2013.

International Search Report and English-language translation thereof issued in PCT/EP2017/066335, to which this application claims priority, dated Dec. 19, 2017.

Written Opinion issued in PCT/EP2017/066335, to which this application claims priority, dated Aug. 28, 2018.

* cited by examiner

SYSTEM AND A METHOD FOR CORRECTIVE LENS DETERMINATION

CROSS REFERENCE TO RELATED APPLICATIONS

This application is a continuation application of international application PCT/EP2017/066335, filed on Jun. 30, 2017, which claims priority to German patent application DE 10 2016 112 023.5, filed on Jun. 30, 2016, both of which are hereby incorporated by reference in their entireties.

TECHNICAL FIELD

The present invention relates to a component, to a system having such a component, and to a kit having such a component and an associated computer program for corrective lens determination, that is to say for measuring a visual defect of an eye.

BACKGROUND

According to Helmut Goersch, Wörterbuch der Optometrie [Optometry dictionary], 2nd edition, published by Bode GmbH & Co. KG, Pforzheim, 2001, page 26, corrective lens determination is the totality of all activities for determining the diopter combination (sphere, cylinder, prism) for correcting visual defects and for determining the near addition in the case of presbyopia. Corrective lens determination comprises a monocular part for determining ametropia (refraction determination) and presbyopia (short-vision lens determination) and a binocular part for determining heterophoria. Corrective lens determination therefore provides data which characterize the vision of the person being examined.

Corrective lens determination is an important part of eye examinations. During such corrective lens determination processes, visual defects are measured and can then be at least partially compensated for with visual aids such as glasses or contact lenses.

In the case of refraction determination, it is possible to distinguish between subjective refraction determination and objective refraction determination. In this case, methods for subjective refraction determination are based on (subjective) feedback from a person to be examined with respect to the person's visual perception. One example in this case is a measurement based on eye charts with an ever decreasing font or ever decreasing symbols, in which case the person to be examined provides feedback with respect to which characters can be discerned by the person. In contrast, methods and apparatuses for objective refraction determination do not require such feedback from the person to be examined with regard to the person's visual perception.

Photorefraction is such an objective refraction method. This method is based on a photo (that is to say an image recording) of light reflection in the pupil of a person. The refractive state can be calculated from the magnitude and position of this light reflection using a mathematical formula. According to Helmut Goersch, Wörterbuch der Optometrie [Optometry dictionary], 2nd edition, published by Bode GmbH & Co. KG, Pforzheim, 2001, page 239, a refractive state should be understood as meaning the state of the optical system of the eye with respect to its index of refraction in relation to its overall length.

W. Wesemann and H. I. Wesemann explain, in "Photorefraktion—Ein objektives Screening-Verfahren zur Refraktionsbestimmung [Photorefraction—An objective screening method for refraction determination]", DOZ—Deutsche Optiker Zeitung, 11/92, pages 50 to 54, that a distinction is made between two physically/optically completely different methods in photorefraction, namely
 1. the "isotropic" photorefraction developed by Howland and Howland (1974), and
 2. the "eccentric" photorefraction presented by Kaakinen (1979).

The "eccentric" photorefraction method is also referred to by other authors as "static photoretinoscopy" (Howland, 1980), "paraxial photorefraction" (Tyler and Noreia, 1985) and "photoretinoscopy" (Schaeffel et al., 1987; Howland, 1985).

W. Wesemann and H. I. Wesemann also state that the first eccentric photorefractometer, which was built by Kaakinen (1979), and also most subsequent devices (Hay et al., 1983; Molteno et al., 1983; Bobier and Braddick 1985; Day and Noreia, 1986; Noreia et al., 1986) comprised a single-lens reflex camera having a lens with a long focal length and a flash device. In contrast to a normal camera, however, the flash in eccentric photorefraction is fastened extremely close to the camera lens. The eccentricity of the light source is in this case the distance between the flash tube (light source) and the entrance pupil of the camera.

If an emmetropic eye is photographed using a flash mounted so close to the camera lens element, red eyes are obtained in the image. If a visually defective eye is photographed, a crescent-shaped light reflection additionally appears in the pupil, from the position and magnitude of which the visual defect can be derived. Further details are gathered from the publications cited above. The eccentric photorefraction method is also described, for example, under the URL roorda.vision.berkeley.edu/photoref.htm, version of Mar. 21, 2016, of Berkeley University.

DE 10 2007 031 923 A1 discloses an apparatus for eccentric photorefraction which uses a scanning light ray. The apparatus may be integrated in a surgical microscope, for example. Therefore, the apparatus described therein is suitable, in particular, for stationary use in doctor's surgeries or hospitals, for example.

A further apparatus for eye examination which can be fundamentally used—with slight modifications if appropriate—for objective refraction determination is described in US 2015/0002817 A1. This is a relatively complicated structure which is likewise predominantly intended for use in doctor's surgeries or clinics.

DE 197 19 694 A1 discloses a further apparatus for objective refraction determination using eccentric photorefraction. In this apparatus, light sources are arranged at different distances from a camera and are permanently installed with the camera in a common housing.

EP 1 308 128 A2 also discloses an apparatus for objective refraction determination using eccentric photorefraction. In this apparatus, all components required may be provided in a compact housing in order to therefore provide a mobile apparatus. A distance between the apparatus and a person to be examined can be determined by means of ultrasonic sensors, by means of optical triangulation, or by means of pattern projection, and this distance is then included in the refraction determination.

In the approaches described above, specially produced apparatuses are used for objective refraction determination and are accordingly expensive.

An attempt has increasingly been made in recent years to provide mobile, cost-effective possibilities for eccentric photorefraction determination. One approach is to use mobile computer apparatuses such as smartphones or tablets. Poster contribution no. D0055 at the ARVO (Association for Research in Vision and Ophthalmology) conference 2014, program no. 436, "Photoscreening for Refractive Error and Strabismus With a Smartphone App", the abstract of which is published under www.arvo.org/webs/am2014/abstract/sessions/114.pdf, proposed carrying out an eccentric photorefraction measurement with a smartphone using an integrated flash of the smartphone and corresponding software (app). Commercial apps of this type for carrying out eccentric photorefraction are also available. Evidence is found, for example, under www.gocheckkids.com/ and www.gocheckkids.com/downloads/Poster_CEI_poster_APOS_Poster2014.pdf.

However, the use of an integrated flash light source of the smartphone may be disadvantageous in such an approach because, for example, the distance between the integrated flash light source and the integrated camera is unfavorable for the photorefraction measurement and/or the integrated flash light source emits in an unfavorable spectral range. In addition, the integrated flash light source is usually only in the form of an individual light source.

The distance between the integrated flash light source and the camera, together with other parameters, determines the measurement range in eccentric photorefraction.

The theoretical measurement range from −D to +D in diopters which can be achieved with an apparatus for eccentric photorefraction is described by the following formula:

$$D = \frac{E}{2ADFR}.$$

In this case, E is the eccentricity of the light source, that is to say the distance between an effective light exit location of the light source and an entrance pupil of the camera. The effective light exit location of the light source is the location from which a light ray emerges in order to illuminate the eye. If the light source and the camera are in a plane perpendicular to the optical axis of the camera, the eccentricity corresponds to the distance between the center of the light source and the entrance pupil of the camera, in which case the center of the entrance pupil (usually on the optical axis of the camera) is used here. In the case of a conventional flash light source of a smartphone, the effective light exit location in this case matches the center of the flash light source. If the light source and the camera are not in such a plane, an offset between the light source and the camera in the direction perpendicular to the plane (vertical offset) is disregarded within the scope of this application. In this case, the vertical offset is typically considerably less than the eccentricity, for example less than 25% or less than 10% of the eccentricity. The eccentricity of the illumination should then be understood as meaning the distance between the optical axis of a camera lens of the mobile computer apparatus, which is intended to record a photo for determining the eccentric photorefraction, and a center of the effective light exit location of the light which is emitted by the light source and is intended to illuminate the person's eye while taking the photo. A is the distance between the eye and the camera. DF stands for the so-called "dark fraction", that is to say the non-illuminated portion of the pupil, or in other words the portion of the pupil. R stands for the radius of the pupil which can likewise be gathered from the recorded image, for example (possibly scaled or normalized on the basis of the determined distance). It should be noted that deviations from this theoretical measurement range may arise in practice depending on the actual eye to be examined. In particular, the measurement range may be asymmetrical in practice.

As is clear from the above formula, the measurement range for a given distance is initially larger, the greater the eccentricity. However, in the case of large measurement ranges, the accuracy with which the eye refraction is determined for visual defects which are small in comparison with D falls, with the result that it may be desirable, for example, to use a smaller eccentricity for illumination. Minor visual defects can therefore be measured in a more accurate manner.

With respect to the use of a smartphone for objective refraction determination, DE 10 2015 100 147 A1 discloses an apparatus having a holder for accommodating a smartphone. The holder may be worn on the head. For objective refraction measurement, an image of the eye is recorded using a camera which is arranged on the same side as a display of the smartphone. This camera is usually referred to as a front camera. For illumination of the eye, different patterns can be displayed on the display of the smartphone. In addition, a light source can be provided in the interior of the holder, the light from which is centrally reflected into the beam path of the camera via a beam splitter.

DE 2 232 410 A discloses a distance measurement apparatus in which a prism generates a beam displacement.

SUMMARY

On the basis of the above-mentioned poster contribution no. D0055 at the ARVO, a first object of the present application is to provide improved possibilities for being able to carry out eccentric photorefraction measurements with an eccentricity which is suitable for such photorefraction measurements using mobile computer apparatuses such as smartphones or tablets.

In a first aspect of the invention, a system, a component, and a method as disclosed herein are provided for this purpose.

Within the scope of the first aspect of the invention, a second object is also to provide light sources for eccentric photorefraction measurement (as are fundamentally known from DE 197 196 94 A1), wherein these light sources are intended to be able to be correctly positioned in a simple manner for an integrated camera of a mobile computer apparatus.

This object is achieved by means of a component as disclosed herein.

Furthermore, a use of such components for photorefraction measurement is provided within the scope of the first aspect of the invention.

On the basis of EP 1 308 128 A2, a third object of the present invention is to provide alternatives to the possibilities mentioned in EP 1 308 128 A2 for measuring distance in photorefraction, which alternatives can be implemented without additional components or only with simpler and more cost-effective additional means than, for example, the ultrasonic sensors or the sample projection apparatus in EP 1 308 128 A2.

In a second aspect of the invention, a method, a computer program, and a mobile computer apparatus are provided for this purpose.

A kit which links the first aspect of the invention to the second aspect of the invention is also provided.

The first aspect of the invention provides a system comprising:

a mobile computer apparatus, wherein the mobile computer apparatus comprises a housing and a camera installed in the housing, characterized by at least one component from the following group:

a component having an optical element for adapting the eccentricity of an integrated light source of the mobile computer apparatus and a fastening element for connecting the component to the housing releasably in a reversible manner, an enclosure element which is dimensioned to completely or partially enclose the mobile computer apparatus and which has at least one light source, wherein the at least one light source is arranged on an outer side of the enclosure element.

The first aspect of the invention also provides a component comprising:

an optical element for adapting the eccentricity of the exit of light from an integrated light source of a mobile computer apparatus, and at least one fastening element for fastening and positioning the component on a housing of the mobile computer apparatus.

Furthermore, the first aspect of the invention provides a component comprising an enclosure element which is dimensioned to completely or partially enclose the mobile computer apparatus. The enclosure element has at least one light source, wherein the at least one light source is arranged on an outer side of the enclosure element.

The optical element can therefore be used to change an eccentricity of the integrated light source of the mobile computer apparatus in order to provide an eccentricity which is suitable for an eccentric photorefraction measurement (as explained at the outset). Alternatively, the enclosure element can be used to easily provide at least one light source having a suitable eccentricity. In addition, the enclosure element can be used to provide a light source for the mobile computer apparatus in a compact manner.

An optical element is therefore an element which influences the propagation of light, for example by deflecting the light, in order to thus adapt the eccentricity. A component in the sense of this application is a part which can be used together with the mobile computer apparatus and comprises such an optical element or an enclosure element.

A fastening element is an element which can be used to fasten and typically also position the component on the mobile computer apparatus. The positioning can be used, in particular, to position the optical element relative to the internal light source, with the result that the optical element receives light from the internal light source. The fastening element may comprise, for example, an adhesive agent such as an adhesive film, a magnetic fastening or else a mechanical fastening, for example in the form of an enclosure element or a bracket. For positioning, an adhesive film or a magnetic fastening may have, for example, a part which is to be mounted on the mobile computer apparatus and has markings for positioning or recesses for elements of the mobile computer apparatus such as the camera or integrated light source, on the basis of which the positioning is carried out. The fastening element may be set up, in particular, to fasten the component to the mobile computer apparatus releasably in a reversible manner. In this case, releasably in a reversible manner means that the component can be removed from the mobile computer apparatus again without destruction and can also be subsequently fastened again.

In this case, an enclosure element is an element which is dimensioned to at least partially enclose the mobile computer apparatus.

Such an enclosure element makes it possible to easily carry out accurate positioning since it is adapted to the dimensions of the mobile computer apparatus. In this respect, it is known to a person skilled in the art that specially adapted enclosure elements are available for different types of mobile computer apparatus (for example smartphones, tablets). In this case, an enclosure element is generally an element in which the mobile computer apparatus can be accommodated, with the result that the enclosure element forms a unit together with the mobile computer apparatus, wherein the outer side of the enclosure element, on which the at least one light source is arranged, forms a visible outer side of this unit or a part (in the case of partial enclosure). This differs from the holder in DE 10 2015 100 147 A1, in which a light source is provided in the interior of the holder and not on an outer side.

In this case, the outer side of the enclosure element should be understood as meaning a side which faces away from the mobile computer apparatus when the enclosure element completely or partially encloses the mobile computer apparatus, that is to say that side of the enclosure element which is in contact with the mobile computer apparatus is the inner side of the enclosure element, and the outer side is accordingly the side facing away from the inner side.

If the enclosure element completely encloses the mobile computer apparatus, the mobile computer apparatus is not visible from the outer side, apart from recesses for components such as an integrated camera. If the enclosure element partially encloses the mobile computer apparatus, parts of the mobile computer apparatus are visible.

Such an enclosure element is typically comparatively thin, that is to say has a short distance between the inner side and the outer side, for example less than 5 mm or less than 3 mm. The enclosure element typically has substantially the same shape as the mobile computer apparatus wherever it completely or partially encloses the mobile computer apparatus, with the result that it encloses the mobile computer apparatus in a substantially form-fitting manner.

A mobile computer apparatus is a device in which typically one or more processors, a memory, a display, and possibly further parts such as interfaces and the like are accommodated in a housing. In this case, the display may be touch-sensitive (for example a so-called touchscreen) in order to therefore also enable inputs. Mobile computer apparatuses which are used within the scope of the present application also comprise a camera installed in the housing. Typical examples of such mobile computer apparatuses are smartphones or tablet PCs or possibly also laptop computers. The computer apparatus is mobile when it can be carried by a person during intended use.

An optical axis usually corresponds to a straight connecting line of all centers of curvature of refractive or reflective surfaces of the imaging optical unit. Light rays on the optical axis pass through the imaging optical unit without deflection. In the case of the camera of the mobile computer apparatus, a camera lens which is used is the imaging optical unit. The optical axis of the camera lens is therefore generally the straight line which matches the axis of symmetry of the camera lens and passes centrally through the entrance pupil of the camera lens.

The illumination emission spectrum should be understood as meaning the spectral distribution of the light emitted by the light source (integrated light source or at least one light source of the enclosure element) and illuminating the eye.

This can be influenced, for example, by a light-emitting means used (for example LED) or an additional preset filter (for example a color filter or a dichroic filter). Within the scope of the present invention, light is understood as meaning electromagnetic radiation in the wavelength range of between 280 nm and 1200 nm. It is known that light in the ultraviolet spectral range can have a damaging effect on the eye.

The spectral distribution is typically selected in such a manner that an amount of light sufficient for the measurement is reflected by the fundus (ocular fundus) (the so-called red reflection) and the measurement provides measured values which are as robust as possible. The provision of a sufficient intensity of red or else infrared radiation is therefore desirable.

In contrast, the person to be measured can be blinded by a high proportion of short-wave (for example blue) light, which results in a reduction in the pupil diameter, which in turn may make the measurement difficult. For this reason, the intensity proportion of ultraviolet or blue radiation is generally kept rather comparatively low, at least in comparison with the intensity proportion of red or infrared radiation.

The fastening element typically comprises an adjustment device for adjusting a position of the optical element relative to the integrated light source of the mobile computer apparatus. Such an adjustment device can be used to accurately position the optical element, for example to adapt it to different positions of integrated light sources in different mobile computer apparatuses. In this case, an adjustment device is a device which can be used to change the position of the optical element.

In this case, the at least one optical element can be set up to receive light which is emitted by the internal light source of the mobile computer apparatus, for example a flash light source integrated in the housing of the mobile computer apparatus or an infrared light source integrated in the housing of the mobile computer apparatus, and is incident on the optical element in a direction of incidence and to output the illumination light offset or offset in a parallel manner with respect to the direction of incidence based on the received light.

A desired eccentricity of the illumination with respect to the lens of the camera used can be set in this manner by selecting the offset between a reception location of the light on an entrance surface into the optical element and an effective light exit location of the light on an exit surface from the optical element.

The at least one optical element may comprise a prism for this purpose. A prism is a geometrical body, the side edges of which are parallel and of equal length, and which has a polygon as a base area. A prism is produced by a parallel shift of a planar polygon along a straight line in space, which is not in this plane, and is therefore a special polyhedron. It is particularly favorable if the prism is in the form of a plane-parallel plate.

The prism can be produced from a glass or plastic material, for example. A plastic prism can be produced in a cost-effective manner, for example, by means of an injection molding method.

Such a prism can be used to deflect light from an installed light source of the computer apparatus in a cost-effective manner to a suitable distance from the camera in preparation for illumination for carrying out eccentric photorefraction.

Instead of a prism, it is also possible to use an optical film which is accordingly set up and has substantially the same function, that is to say a film in which light from the light source is deflected at boundaries with a refractive index jump inside the film or between the film and the environment of the film by means of refraction or reflection in order to set an offset and therefore a desired eccentricity.

In one exemplary embodiment, the at least one optical element has a light entrance surface which is set up to receive light emitted by the integrated light source of the mobile computer apparatus and a light exit surface which is set up to output the received light. The optical element is also designed such that the received light is always output at the same location of the light exit surface within a tolerance range of less than 1 mm or less than 0.5 mm irrespective of the location at which the light emitted by the integrated light source of the mobile computer apparatus has been received by the light entrance surface.

This makes it possible to determine an effective position and axis of the illumination relative to a camera of the mobile computer apparatus and therefore the eccentricity irrespective of an exact position of the installed light source of the mobile computer apparatus, for example a flash.

In this case, such an optical component of the described type typically comprises a multiplicity of first refractive or reflective surfaces, for example prism surfaces, which are assigned to the light entrance surface and are inclined such that they guide light received via the light entrance surface in an identical direction, for example deflect it by approximately 90°. In this case, a prism surface is a surface of a prism at which a refractive index jump (between the prism and the environment, for example air or another material) takes place and the refraction is therefore reflected, which deflects the light. Structure sizes of such first surfaces may be less than 1 mm, or else greater than the latter. In this case, the optical component also comprises a second refractive or reflective surface in order to guide the light deflected by the first refractive or reflective surfaces to the light exit surface, for example to again deflect it by approximately 90°. In the case of prism surfaces, the arrangement of first surfaces can be referred to as a micro-prism array.

Instead of the above-described structures having the refractive or reflective first and second surfaces, diffractive structures and elements having such diffractive structures (referred to as diffractive elements for short) can also be used to deflect the light. Diffractive structures typically have such small structures sizes, for example in the range of the wavelength of the light, that diffraction effects occur. Suitable configuration of the diffractive structures makes it possible to deflect light by means of diffraction at an angle determined by the configuration of the structures.

Diffractive structures can typically be provided in the form of a hologram, for example in the form of a volume holographic grating. In order to produce such a volume holographic grating, a light-sensitive material is illuminated with at least two interfering coherent light waves, for example as is known per se, wherein one light wave comes from a direction corresponding to the position of the light source of the mobile computer apparatus and the other light wave comes from a direction corresponding to a desired deflection direction into which the light from the light source is intended to be deflected. The light-sensitive material is then developed.

Such an optical component which can be produced in a favorable manner makes it possible to easily forward light which is received in the region, for example from different possible positions of installed illumination or a mobile computer apparatus.

The at least one light source of the enclosure element may comprise, for example, one or more light-emitting diodes (LEDs), one or more organic light-emitting diodes (OLEDs) or one or more quantum dot light source elements.

Providing one or more light sources in the component makes it possible to easily determine, for example, a desired spectral range of the illumination and/or a desired effective light exit location of the illumination and therefore the eccentricity. A form of the illumination or illumination from different directions can also be easily achieved.

The light sources can be supplied, for example, by a rechargeable battery arranged in the component. The light sources can also be supplied via a power supply of a mobile computer apparatus, for example by means of corresponding wired coupling to an interface of the mobile computer apparatus (for example a USB interface).

For example, the at least one light source of the enclosure element may be an infrared light source. This has the advantage that the pupil of an eye to be examined is not constricted by the illumination and a fundus reflectivity of the eye, that is to say a reflection of the light at the ocular fundus, is subject to individual fluctuations to a lesser extent.

In particular, the at least one light source of the enclosure element may comprise a multiplicity of light sources arranged in a wedge-shaped manner. Illumination using such light sources arranged in a wedge-shaped manner makes it possible to linearize a reflection form on the basis of the refraction of the eye since it has been shown that the intensity distribution of the red reflection has a linear profile in the case of such wedge-shaped illumination on the basis of a visual defect of the person to be examined. This can facilitate the evaluation of recorded images of the eye for refraction determination since in this case the gradient of this linear profile can simply be evaluated. This approach is explained in more detail under the URL of Berkeley University mentioned at the outset with reference to Schaeffel, F., Farkas, L. & Howland, H. C. (1987) Infrared photoretinoscope. Appl. Opt. 26, 1505-1509.

The at least one light source of the enclosure element may comprise a plurality of light sources to be arranged at different distances from the camera of the mobile computer apparatus. A desired eccentricity of the illumination can thus be set by accordingly activating different light sources, which, as explained at the outset, can be used to set a desired measurement range in the case of a particular distance between the eye and the camera.

The component may comprise a filter for filtering the illumination light and/or a filter for filtering light intended for an integrated camera of the mobile computer apparatus.

This makes it possible to determine a spectrum desired for a refraction measurement by accordingly selecting the filter, in particular a spectrum at least predominantly in the red and/or infrared range, as explained further above.

The enclosure element may comprise an opening for a camera of the mobile computer apparatus, wherein the at least one light source can be arranged adjacent to the opening in such a manner that there is a desired eccentricity, for example between 5 mm and 20 mm, for example in order to achieve a desired measurement range of, for example, between −2 and 2 diopters or between −5 and 5 diopters (in which case minor visual defects possibly cannot then be measured) for a particular distance (for example in the range of 40-60 cm), as explained at the outset, wherein the measurement range can be adapted, in particular, to a person to be examined. This makes it possible to accurately position the light source relative to the camera by aligning the opening with the camera. In other words, the opening is arranged on the mobile computer apparatus in such a manner that the camera can record images through the opening.

The first aspect of the invention also provides a method for corrective lens determination, comprising:
illuminating a person's eye with light from an integrated light source of a mobile computer apparatus,
i) recording an image of the person's eye using a camera of the mobile computer apparatus, and
ii) carrying out eccentric photorefraction determination based on the recorded image,
iii) characterized by
iv) adaptation of an eccentricity of the light to an eccentricity for the eccentric photorefraction determination.

Adapting the eccentricity, for example by means of the optical element described above, makes it possible to set a suitable eccentricity for the eccentric photorefraction determination, as already described above.

As generally explained at the outset for corrective lens determination, the eccentric photorefraction determination provides data which characterize the vision of the person, for example as spherocylindrical refraction (sphere, cylinder, axis position, as defined in DIN EN ISO 13666:2012). On the basis of these data, an ophthalmologist, for example, can then make a diagnosis, for example whether the person is long-sighted or short-sighted, and can prescribe a corresponding treatment, for example the wearing of glasses. This diagnosis is not the subject matter of the present application and the claimed methods provide only the data which can then be used for the diagnosis.

The eccentricity can be adapted to the desired eccentricity within a tolerance range irrespective of a position of the integrated light source, as already described above for some optical elements. In this manner, the method can be set to the same eccentricity despite varying positions of the integrated light source (for example in different types of mobile computer apparatus).

The second aspect of the invention carries out a method for corrective lens determination, comprising the following steps: Determining (that is to say ascertaining and/or establishing) a distance between the mobile computer apparatus and a user's head,
recording an image of an eye of the user's head, and carrying out corrective lens determination based on the recorded image and the distance.

In this case, the image can be repeatedly recorded with different illumination directions. A plurality of meridians are measured as a result, that is to say the eye is measured along different directions. This makes it possible to determine parameters such as sphere, cylinder and axis.

As a result of such a computer program, a mobile computer apparatus such as a smartphone can be used for eccentric photorefraction. Determining the distance makes it possible to determine a desired distance and therefore to determine a desired measurement range for a given eccentricity according to the relationship between the measurement range, distance and eccentricity explained at the outset.

As already mentioned, eccentric photorefraction can be used in exemplary embodiments to carry out the corrective lens determination. Even if the corrective lens determination of an eye is discussed here, "a(n)" should be considered merely as an indefinite article here, and it goes without saying that both eyes of a person can be examined. So-called red reflection, that is to say light reflected by the fundus of the eye, is produced in this case by eccentric illumination which can be produced by means of one of the above-described variants of a component. This red reflection is visible in the recorded image(s). If the person has ametropia (visual defect, that is to say hypermetropia, myopia or astigmatism), this results in inhomogeneous illumination of the pupil. In the case of an emmetropic (normally sighted) eye, the pupil appears dark. The light distribution can be evaluated using image analysis methods and the visual defect of the person can be determined on the basis of the light distribution. Mathematical formulas, as described in the literature and explained briefly later, are used for this purpose. It should be noted that, in the case of unfavorable eccentricity of the illumination, the pupil may appear dark even in the case of ametropia (visual defect). However, a desired eccentricity can be set using the optical components described.

According to the invention, the determination of the distance comprises one or more of the following steps in this case:

recording an image of an object having known dimensions, and determining the distance based on the recorded image, determining the distance based on an autofocus setting of a camera of the mobile computer apparatus,
determining the distance based on a recording of the mobile computer apparatus via a mirror,
setting an autofocus to a predefined distance value and outputting a message if a distance of the head corresponds to the predefined distance value,
receiving an input from the user, and
estimating an arm length of the user and determining the distance based on the estimated arm length.

The predefined distance value is in this case a distance value which is desired or required for eccentric photorefraction determination based on the relationships between the measurement range, eccentricity and distance which were explained at the outset.

There are therefore a multiplicity of simple possible ways of determining the distance. These are carried out using components which are either present anyway (such as the autofocus of the camera) or using cost-effective components such as an object of known dimensions or a mirror.

A computer program having a program code which, when executed on a processor, carries out the above method is also provided.

Such a computer program may be provided, for example, for downloading to the mobile computer apparatus from a network. Such computer programs for mobile computer apparatuses are also referred to as apps. During recording, the eye can be illuminated in this case using one or more of the components described above. The computer program can also be stored on a computer-readable medium.

A mobile computer apparatus having a processor and a data storage medium (for example a memory), which stores such a computer program, is also provided.

A kit which links the first aspect of the invention and the second aspect of the invention is also provided.

Such a kit makes it possible to provide a cost-effective possible way of using a mobile computer apparatus such as a smartphone or a tablet for the refraction measurement by mounting the component on the mobile computer apparatus, for example, and executing the computer program on the mobile computer apparatus.

BRIEF DESCRIPTION OF THE DRAWINGS

The disclosure will now be described with reference to the drawings wherein.

DESCRIPTION OF EXEMPLARY EMBODIMENTS

Exemplary embodiments discussed below relate to a component for a mobile computer apparatus, in particular for mounting on a housing of the mobile computer apparatus. In the following description, smartphones are used as examples of such mobile computer apparatuses. Systems according to the invention which are explained below comprise a smartphone and a component according to the invention which is used to illuminate an eye of a person to be examined. As an alternative to such smartphones, other mobile computer apparatuses such as tablet PCs or laptop computers can also be used.

Figure 1:
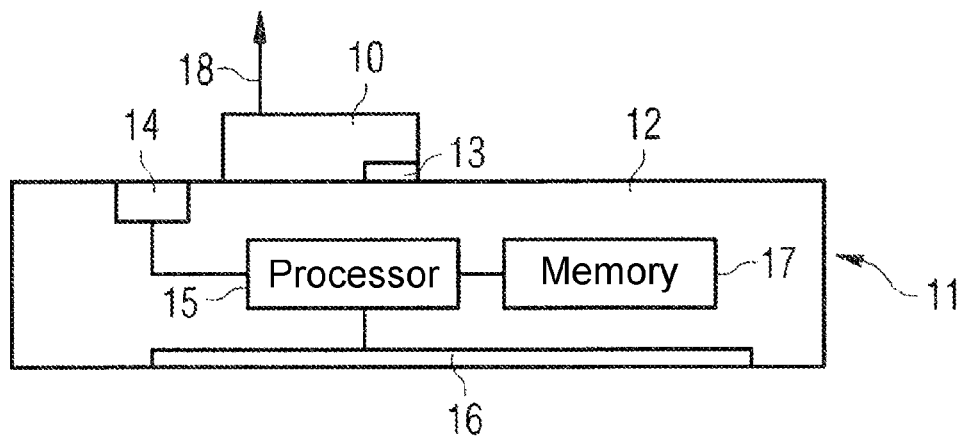
FIG. 1 shows a schematic illustration of a system in accordance with one exemplary embodiment.

FIG. 1 shows a schematic illustration of a system in accordance with one exemplary embodiment. The system in FIG. 1 comprises a mobile computer apparatus 11 and a component 10 mounted on a housing 12 of the mobile computer apparatus 11. The mobile computer apparatus 11 has a processor 15 arranged in the housing 12 and an associated memory 17. The memory 17 can store, in particular, programs which, when they run on the processor 15, cause a method for corrective lens determination of an eye of a person to be examined to be carried out using eccentric photorefraction.

The mobile computer apparatus 11 also comprises a camera 14 which is installed in the housing 12 and can be used to record one or more images of a person to be examined, in particular of one or both eyes of the person. The mobile computer apparatus 11 also comprises a display 16 which is used to output results of the refraction measurement, for example. The display 16 can also be in the form of a so-called touchscreen and can enable inputs by a user.

The illustrated parts of the mobile computer apparatus 11 should not be interpreted as restrictive, and further (conventional) parts of mobile computer apparatuses such as smartphones, tablet PCs or laptops can be provided, for example interfaces, keyboards, communication devices for communicating with a network (wireless or wired), mass memories such as hard disks and the like.

The component 10 is mounted on the housing 12 of the mobile computer apparatus 11 via a fastening element 13.

The component 10 is set up to output illumination light for illuminating the person's head, in particular the eye, as indicated by an arrow 18. As will be explained in more detail below on the basis of various specific exemplary embodiments, the component 10 can use, for example, light from an installed light source of the mobile computer apparatus 11 and can suitably deflect and/or filter the light in order to produce the illumination light 18. Such installed light sources may be flash light sources, for example. In other variants, the component 10 may comprise an enclosure element having one or more light sources in order to produce the illumination light 18.

In this case, in some exemplary embodiments, the processor 15 can control the illumination light 18 in such a manner that the illumination is carried out in a manner matched to an image recording using the camera 14. In other exemplary embodiments, the component 10 may comprise, for example, a switch or the like which can be used to switch the illumination on and off. Recorded images are finally evaluated by means of the processor 15 for corrective lens determination.

Various possible implementations for the component 10 are now explained with reference to FIGS. 2-6. In order to avoid repetitions, identical or mutually corresponding elements have the same reference signs in FIGS. 2-6 and are not repeatedly explained. In this case, a smartphone 20 is used as an example of a mobile computer apparatus in FIGS. 2-6. However, the illustrated variants of the component 10 can also be accordingly used together with other mobile computer apparatuses, for example tablet computers.

Figure 2:
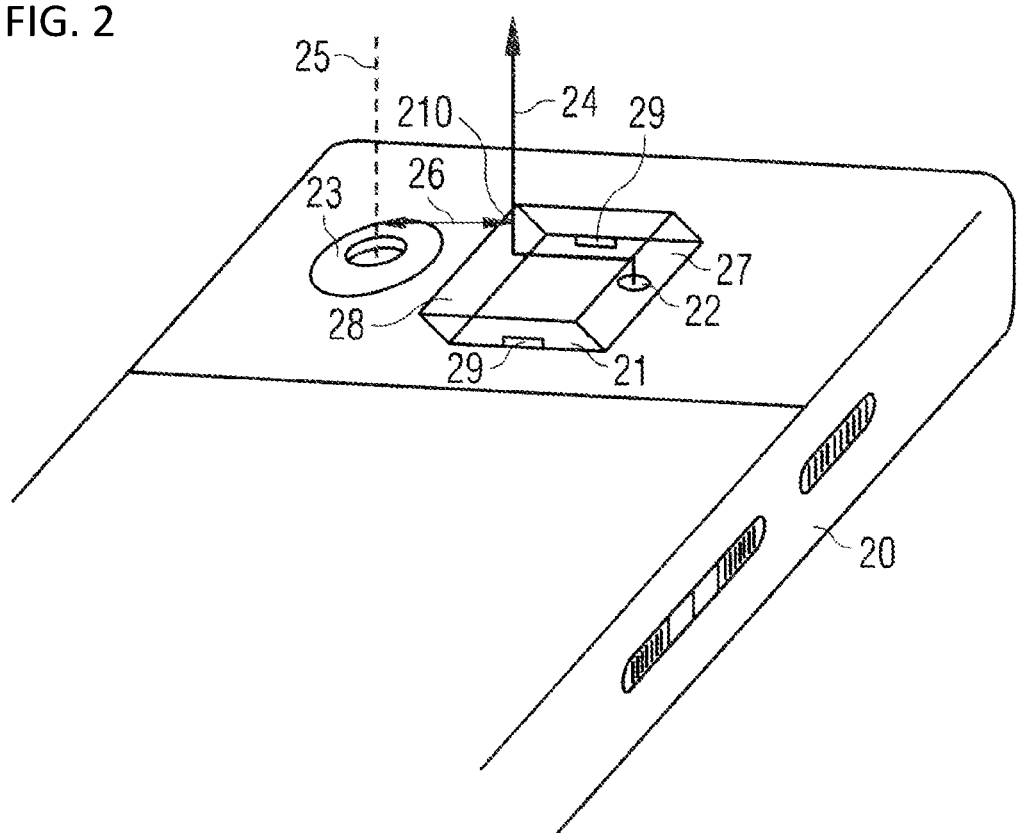
FIG. 2 shows a perspective partial view of a system in accordance with one exemplary embodiment.

FIG. 2 shows a perspective partial view of a system comprising a smartphone 20 and a component 21 in accordance with a second exemplary embodiment. The smartphone 20 has a light source 22 integrated in the housing and a camera 23 integrated in the housing on the rear side, which light source and camera are arranged at a distance of 10 mm from one another, for example. For carrying out eccentric photorefraction using the integrated light source 22 and the integrated camera 23, this smartphone 20 is not suitable for all distances and measurement ranges on account of the inherent eccentricity of 10 mm. If the smartphone is held at a distance of 60 cm from an eye to be examined, for example, a measurement range of approximately −5 to +5 diopters results, but minor visual defects in the range of approximately −1 to 1 diopter cannot be measured. On the other hand, greater distances are difficult to achieve, at least when the person to be examined is himself holding the smartphone 20, on account of the limited arm length. Therefore, a component 21 according to the invention is mounted on the rear side of the smartphone 20 (that is to say a side facing away from the display of the smartphone) in the system in FIG. 2. In this case, the component 21 is positioned and configured in such a manner that it changes the eccentricity of the illumination to a desired value.

In the exemplary embodiment shown in FIG. 2, the component has a prism 21 for this purpose, more precisely a plane-parallel plate having reflection surfaces 27, 28 which are arranged parallel to one another on an end face as an optical element which, in the exemplary embodiment illustrated, is mounted on the housing of the smartphone 20 by means of adhesive strips 29. The prism 21 deflects light which is emitted by an internal light source 22 of the smartphone 20, as illustrated in FIG. 2, by first of all reflecting the light emitted by the light source 22 at the reflection surface 27, as illustrated, and then at the reflection surface 28 in order to emit illumination light 24 at a desired distance from a camera 23 of the smartphone 20.

It is therefore possible to provide a desired eccentricity 26 of the illumination for a photorefraction measurement, which eccentricity corresponds to the distance between an effective light exit location 210 of the illumination light 24, which is offset with respect to the light source 22 by the prism 21, and the camera 23 (depicted here with respect to a central axis corresponding to the optical axis 25 of the camera). As explained at the outset, the eccentricity 26 is measured here from the light exit location 210 to the optical axis 25 of the camera 23. A vertical offset between the light exit location 210 and the camera 23, that is to say an offset in a direction parallel to the optical axis 25 (here a direction perpendicular to the surface of the smartphone 20), is disregarded when determining the eccentricity. In this respect, it is typical for the prism 21 to be so thin (in a direction parallel to the optical axis 25) that this vertical offset is considerably smaller than the eccentricity 26. The eccentricity 26 may be 5 mm, for example, which results in a measurement range of approximately −2.5 to +2.5 diopters for a distance of 60 cm.

In the exemplary embodiment illustrated, the light source 22 is a light source which is also used as illumination for recordings with the camera 23 during other operation of the smartphone 20. It may be, for example, a flash light source for photos or a continuous light source (for example based on light-emitting diodes) for video recordings using the smartphone 20.

The light source 22 may also be an infrared light source which is used, for example, for a sensor of the smartphone 20. Such an infrared light source 22 may also be arranged further away from the camera 23. In this case, the component 30 is then dimensioned accordingly in order to achieve a deflection with respect to a desired eccentricity, for example 5 mm, as described above. The value of 5 mm should be understood only as an example here, and other values, for example between 5 mm and 20 mm, can also be achieved by accordingly dimensioning the prism 21 depending on the desired working distance and the desired measurement range.

In this case, the prism 21 may be produced from a glass or a plastic material, which enables cost-effective production. Such a plastic prism can be produced using an injection molding method, for example. The exemplary embodiment in FIG. 2 therefore makes it possible to provide a respectively desired measurement range for the eccentric photorefraction in a cost-effective manner for a given distance between the person to be examined and the smartphone 20.

The prism 21 is therefore set up to provide a desired eccentricity for a particular model of the smartphone 20 which has a particular distance between the light source 22 and the camera 23. In this case, different prisms can be offered for different types of smartphone 20.

Figure 3:
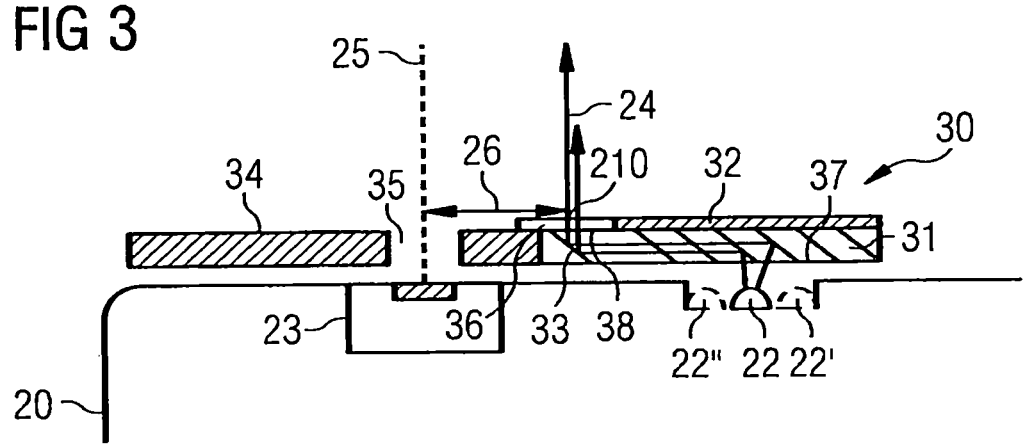
FIG. 3 shows a partial cross-sectional view of a system in accordance with one exemplary embodiment.

FIG. 3 shows a partial cross-sectional view of a system in accordance with a further exemplary embodiment. The system comprises the smartphone 20 and a component 30 according to the invention which, like the component in FIG. 2, is mounted on the rear side of the smartphone 20.

The component 30 according to the invention shown in FIG. 3 is set up in such a manner that it can produce a desired eccentricity 26 of a light exit location 210 with respect to the optical axis 25 of the camera 23 for different positions of an installed light source of the smartphone 20 (the explanations with respect to the eccentricity 26, as measured between the light exit location 210 and the optical axis 25, made with reference to FIG. 2 also apply to the exemplary embodiment in FIG. 3). The component 30 comprises a carrier material 34 having a recess 35 for the camera 23 of the smartphone 20. An arrangement 31 of first reflective surfaces and a second reflective surface are incorporated in the carrier 34. In the example illustrated, the arrangement 31 is a microprism array and the first reflective surfaces are prism surfaces.

Light from the light source 22 passes through an entrance surface 37 to the arrangement 31 and is deflected by one or more of the first reflective surfaces by approximately 90° in the direction of the second reflective surface 33. A deflection by approximately 90° is again effected at the second reflective surface 33, as illustrated in FIG. 3, with the result that the light ray is output through an exit surface 38 as the illumination light 24 with the eccentricity 26. However, other geometries with other angles are also possible.

In this case, the eccentricity 26 is substantially, for example with a tolerance of less than 1 mm or less than 0.5 mm, independent of the exact position of the light source 22. For elucidation, FIG. 3 illustrates other possible light sources 22' and 22" which are offset with respect to the light source 22. In the case of these light sources 22', 22" as well, light from the light source 22' or 22" is deflected via the arrangement 31 toward the second reflective surface 33 and is again deflected by the latter, with the result that substantially the same eccentricity 26 of the illumination light 24 with respect to the optical axis 25 of the camera 23 always results irrespective of the exact position of the light source.

In the example illustrated, the carrier 34 is in the form of a film which has an adhesive surface on one side in order to thus be able to easily fasten the optical component 30 to the smartphone 20. The reference sign 32 is used to denote an opaque cover which prevents light, for example stray light, emerging from the component 30 at locations other than the location intended for the illumination light 24.

In the exemplary embodiment illustrated in FIG. 3, the component 30 has an optical filter 30, namely a chromatic bandpass filter, in order to restrict the emission spectrum of the light source 22 to a desired spectrum, for example a spectrum predominantly in the red and/or infrared range, as explained at the outset. In the example illustrated, the filter 30 is arranged on the light exit surface 38. However, such a filter may also be arranged at other locations in the beam path, for example between the arrangement 31 and the second surface 33, or else on the light entrance surface 37.

Figure 10:
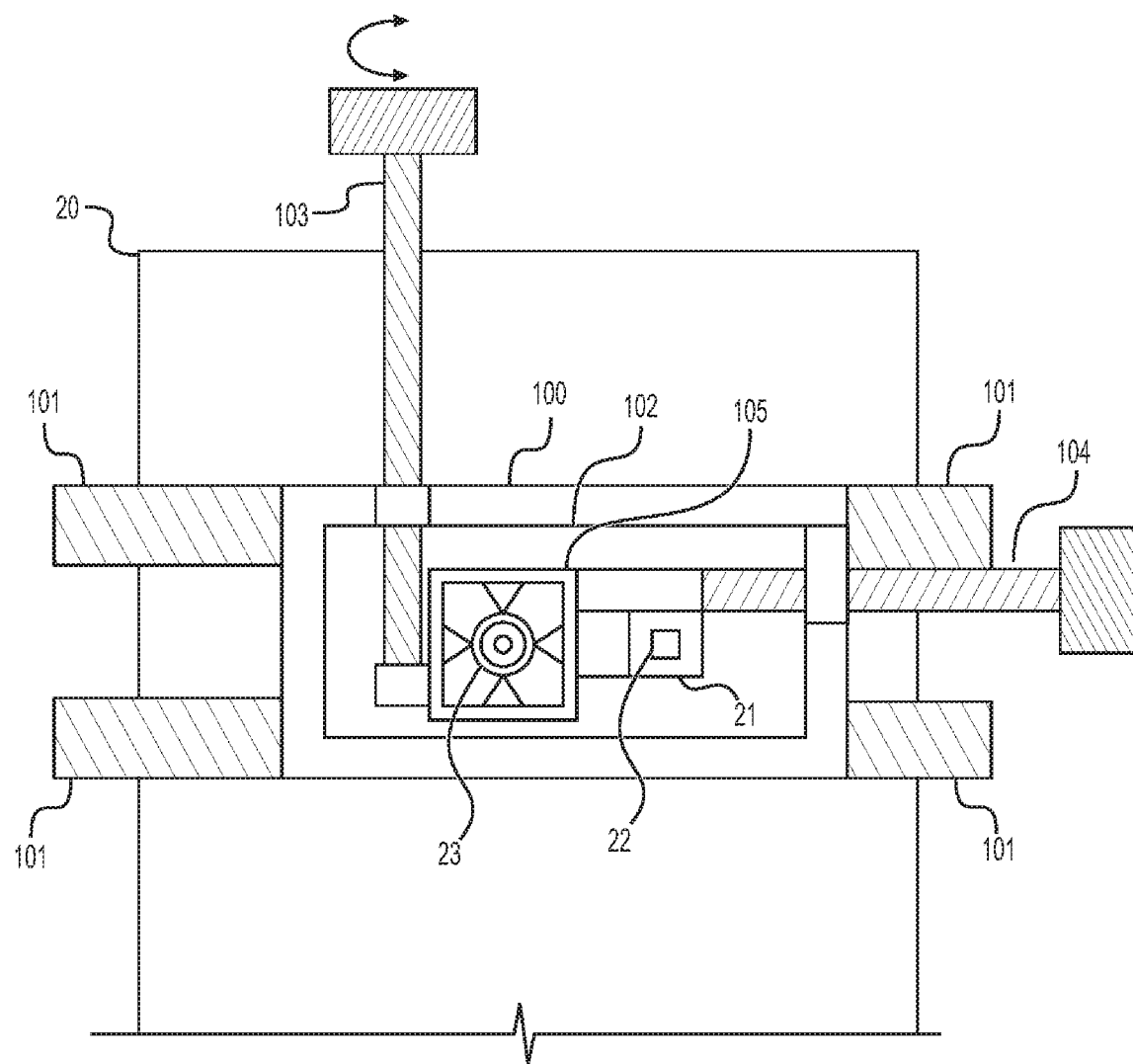
FIG. 10 shows a system in accordance with a further exemplary embodiment.

FIG. 10 shows a system in accordance with a further exemplary embodiment which illustrates a further possibility for fastening the prism 21 to the smartphone 20. In this case, the system in FIG. 10 has a plate 100 which is fastened to the smartphone 20 releasably in a reversible manner by means of brackets 101. A further plate 102 is arranged on the plate 100 and can be moved and positioned relative to the plate 100 by means of setting screws 103, 104. The prism 21 is fastened on the further plate 102.

The plates 100, 102 have a recess 105 for the camera 23 of the smartphone 20. The plates 100, 102 also have a recess for the integrated light source 22.

The prism 21 can be positioned relative to the integrated light source 22 by moving the plate 102 via the setting screws 103, 104, with the result that light from the light source 22 strikes the surface 27 of the prism (see FIG. 2).

In the exemplary embodiments discussed above with reference to FIGS. 2 and 3, light from a light source 22 of the smartphone 20 is deflected in order to provide illumination light 24 having a desired eccentricity 26. In the exemplary embodiments described below and shown in FIGS. 4 to 6, the respective component itself has one or more separate light sources.

Figure 4:
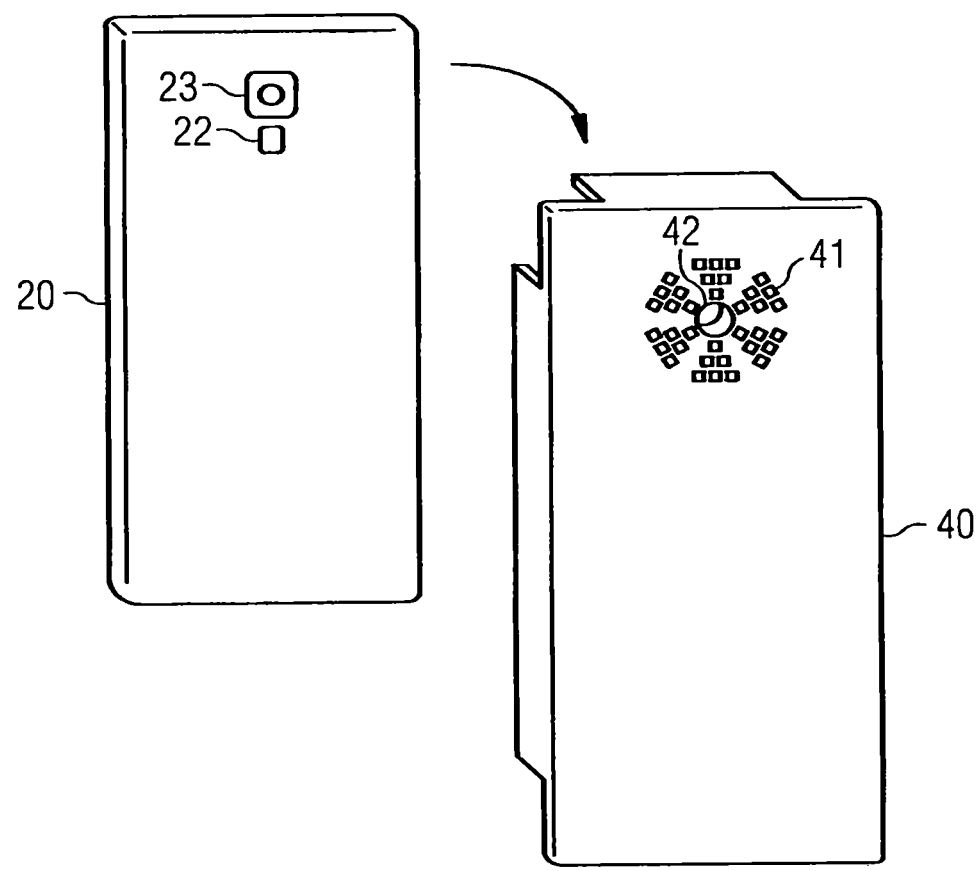
FIG. 4 shows an illustration of a system in accordance with a further exemplary embodiment.

The exemplary embodiment in FIG. 4 shows a perspective view of a system in accordance with a further exemplary embodiment having the smartphone 20 and a component which is in the form of an enclosure element 40.

The enclosure element 40 comprises a multiplicity of light sources 41. The multiplicity of light sources 41 are arranged in a plurality of wedge-shaped arrangements around an opening 42 in the enclosure element 40 which is used as a fastening element. The light sources 41 are, for example, light-emitting diodes (LEDs), organic light-emitting diodes (OLEDs) or quantum dot light source elements. The enclosure element 40 is adapted to the shown type of smartphone 20 in such a manner that the smartphone 20 can be inserted into the enclosure element 40 and in the process the camera 23 of the smartphone 20 is aligned with the opening 42. In this case, the light sources 41 are arranged on the outer side of the enclosure element 40, that is to say on the side facing away from the smartphone 20, when the smartphone 20 has been inserted into the enclosure element 40. In this manner, the light source 22 of the smartphone is shaded and is replaced as it were by the light sources 41 in the example illustrated. The light sources 41 can provide illumination with a desired eccentricity with respect to the camera 23. The eccentricity can also be set by using a plurality of light sources, as in FIG. 4. The arrangement in the shape of a wedge also makes it possible to linearize the red reflection in the pupil, as already described further above. It should be noted that an enclosure element, like the enclosure element 40, can also be used to fasten the optical components in FIGS. 2 and 3 to a mobile computer apparatus such as a smartphone.

The light sources 41 can emit light in the visible range, but may also be infrared light sources with emission of light below the visible range in the infrared range. The latter has the advantage that the person to be examined is disturbed to a lesser extent and the pupil of the eye to be examined is also not constricted or is constricted less on account of the illumination by means of light from the light sources 41. In this case, an infrared filter (not explicitly shown in FIG. 4) is provided in the opening 42 and allows only the infrared light to pass.

The light source elements 41 are supplied by a rechargeable battery arranged in the enclosure element 40. The light source elements 41 are controlled in a wired or wireless manner (for example via Bluetooth or NFC (Near Field Communication)) via the smartphone 20. In other implementations, control with a switch provided in the enclosure element 40 or another operating element is also possible.

Figure 5:
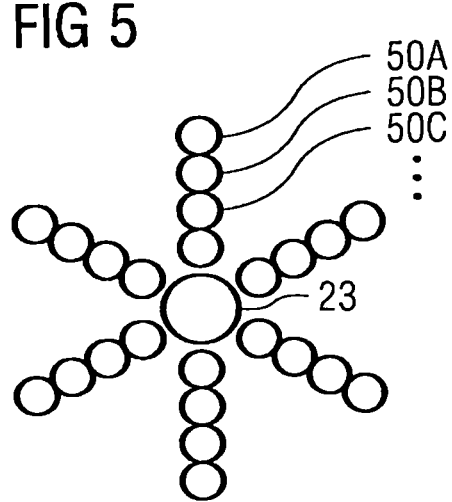
FIG. 5 shows an illustration of a light source arrangement which can be used in components in accordance with some exemplary embodiments.

Arrangements of light source elements or enclosure elements other than those illustrated in FIG. 4 are also possible. FIG. 5 shows a system comprising a smartphone, only the camera 23 of which is illustrated in FIG. 5, and a component having an optical element in which a multiplicity of light source elements 50A, 50B, 50C, . . . are provided. The light source elements 50A, 50B, 50C, . . . may be arranged, for example, in an enclosure element such as the enclosure element 40 in FIG. 4. In the exemplary embodiment in FIG. 5, a plurality of light source elements 50A, 50B, 50C, . . . are each arranged at a particular angle in a row. A desired eccentricity can be achieved by selectively switching on the light source elements 50A, 50B, 50C, . . . . In the case of four light source elements, they may be arranged at distances of 5 mm, 10 mm, 15 mm and 20 mm, for example. In this case, as already explained, each eccentricity is assigned to a defined measurement range, in which an eccentric photorefraction measurement is possible, for a given distance between the smartphone and the person to be examined. With the numerical example above, a total measurement range of between approximately −9 and +9 diopters can be covered by gradually using the four light source elements at a distance of 60 cm between the smartphone and the eye.

The light source elements 50A, 50B, 50C, . . . can emit light in the visible and/or infrared range, as already explained with reference to FIG. 4.

Figure 6:
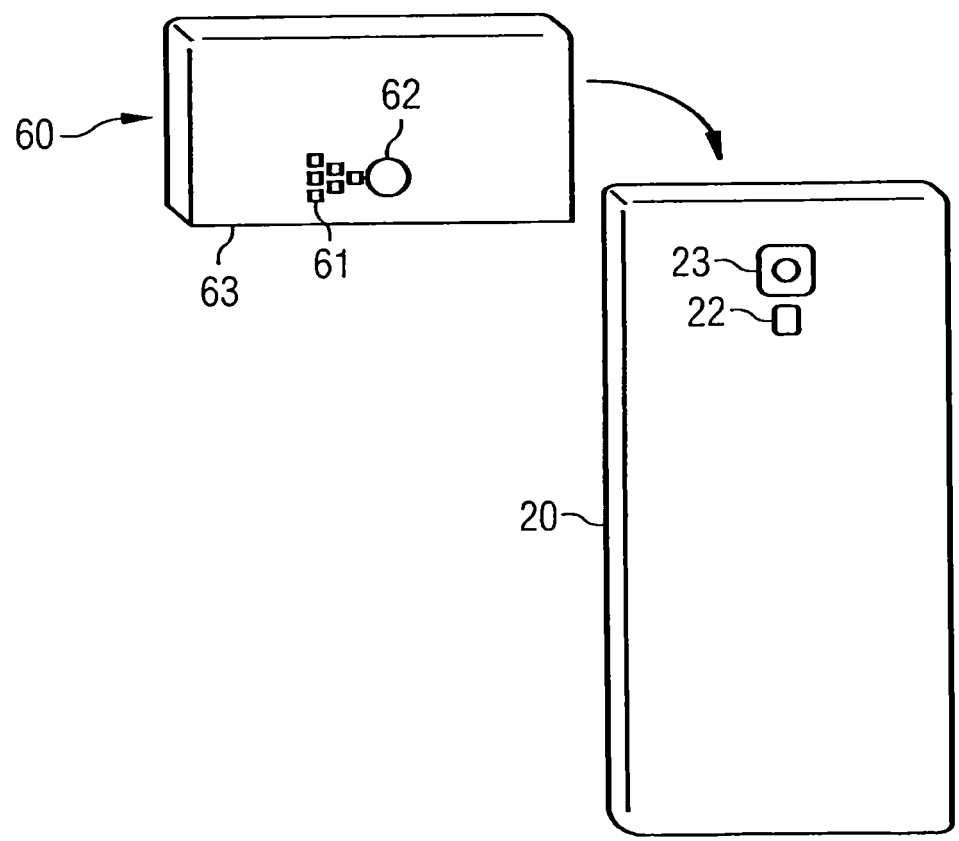
FIG. 6 shows a system in accordance with a further exemplary embodiment.

FIG. 6 shows a system having the smartphone 20 and a component 60. The component 60 comprises an enclosure element 63 and light source elements 61 which are mounted adjacent to an opening 62 in an enclosure element 63. In the exemplary embodiment in FIG. 6, the enclosure element 63 is in the form of a cap and is adapted, in terms of size and shape, to the smartphone 20 such that it can be "placed on" the smartphone 20. In this case, in a similar manner to the exemplary embodiment in FIG. 4, the opening 62 is aligned with the camera 23 of the smartphone, and the internal light source 22 of the smartphone 20 is covered. In contrast to FIG. 4, only a single wedge of light source elements 61 is present in the exemplary embodiment in FIG. 6. However, it is also possible to provide a plurality of such wedges in a similar manner to FIG. 4 or an arrangement like in FIG. 5. This shows, in particular, that various configurations of enclosure elements are possible and can be combined with different arrangements of light sources. As already explained with reference to FIG. 4, the light source elements 61 can also operate in the visible or infrared range, in which case a corresponding infrared filter can be provided in the opening 62, as already explained for the exemplary embodiment in FIG. 4. It should be noted that the enclosure elements 40 and 63 in FIGS. 4 and 6, instead of having light source elements, can also be combined with the prism 21 in FIG. 2 or the component 30 in FIG. 3 in order to mount them on the smartphone 20 and position them. In this manner, the prism 21, for example, can be positioned relative to the internal light source 22 of the smartphone 20 by means of the enclosure element in order to adapt the eccentricity, as shown in FIG. 2. For this purpose, the enclosure element may then have an opening at the position of the internal light source 22, above which the prism 21 is arranged.

Figure 7:
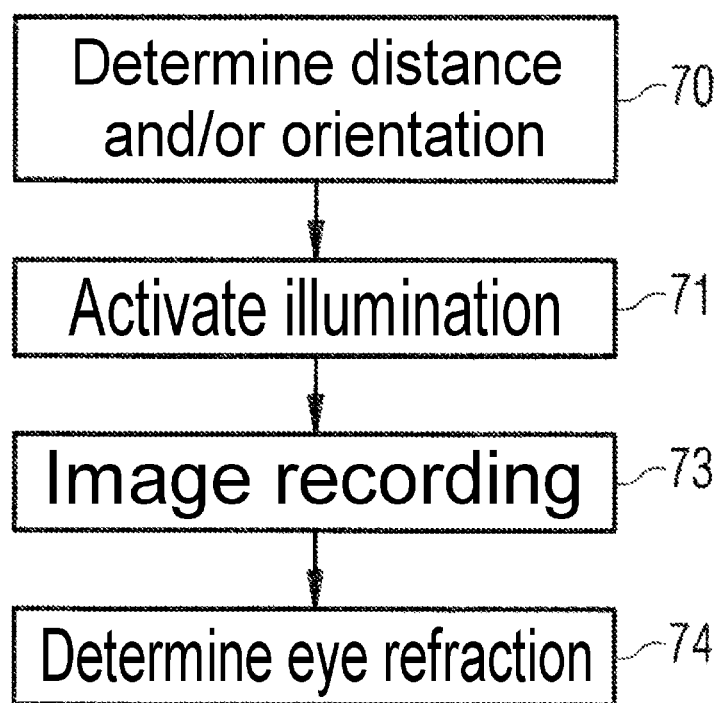
FIG. 7 shows a flowchart for elucidating a method in accordance with one exemplary embodiment.

It is now explained below how corrective lens determination can be carried out with the aid of one of the systems comprising a mobile computer apparatus and a component discussed above. In this respect, FIG. 7 shows a flowchart of a corresponding method in accordance with one exemplary embodiment. In this case, the method can be carried out in a manner controlled by the mobile computer apparatus, for example by means of a computer program (usually referred to as an app in the case of smartphones or tablets) which is stored in a memory of the mobile computer apparatus (for example the memory 17 in FIG. 1), is executed on a processor (such as the processor 15) and therefore controls the method sequence.

As already explained above, the measurement range of the eccentric photorefraction measurement is dependent on the eccentricity of the illumination, the pupil diameter and the distance between the head of the person to be examined and the camera. Therefore, in step 70 of the method in FIG. 7, the distance between the mobile computer apparatus, for example the smartphone 20 in the above exemplary embodiments, and the person's head is first of all determined (measured and/or established), and/or the person is instructed to position, for example hold, the mobile computer apparatus at a particular distance from the head. Such a distance measurement or the establishment of the distance between the mobile computer apparatus and the person's head can be carried out in the following manner, for example.

In step 70, an object of known size can be moved into the vicinity of the person's face and a corresponding image can be recorded using the camera. This image may be the same as that used for the corrective lens determination. In this case, the distance is not determined in a step beforehand, but rather together with the recording of the image. The distance can then be determined from the size of the object in the image. However, such a distance determination is also possible before the recording of the image, on the basis of which the corrective lens determination is carried out. A credit card or another object which has a standardized or known size can be used as the object of known size, for example. An object having defined dimensions can also be specifically provided for the measurement, for example. Such an object of known size can then also be used as a benchmark for further purposes, for example for determining dimensions in the recorded image, for example the pupil size.

A focusing device of the camera of the mobile computer apparatus (autofocus) can also be used to determine the distance in step 70. In smartphones such as the smartphone 20 or similar computer apparatuses, the cameras often have such an autofocus. The distance is concomitantly determined during focusing by means of this autofocus, and this distance determination can then also be used for the method according to the invention. In this manner, hardware which is already present is used to determine the distance.

In another variant, the above-mentioned autofocus of the camera of the mobile computer apparatus can be set to a fixed distance desired for the refraction measurement in step 70. The mobile computer apparatus can then provide positive feedback if the facial part, in particular the eyes, of the user is imaged sharply and the user is therefore at the desired distance. The distance can be determined in a relatively simple manner in this way.

A distance sensor (also referred to as a depth sensor) which is explicitly present or a stereo camera system, if present in the mobile computer apparatus anyway, can also be used to determine the distance in step 70. Such distance sensors may comprise infrared sensors, time-of-flight sensors and the like, for example.

In another variant, a mirror can be used to record the user's face, that is to say the user is not recorded directly, but rather via a mirror. In such a case, the user can be instructed in step 70 to hold the mobile computer apparatus directly beside his face for image recording, with the result that the mobile computer apparatus is photographed together with the face in the mirror. In this case, the mobile computer apparatus, for example the smartphone, can then itself be used as a size scale (similar to the case above in which a particular object is recorded) since the dimensions of the mobile computer apparatus are known.

In yet another exemplary embodiment, the user to be examined or a person carrying out the examination can be requested in step 70 to manually input the distance to the mobile computer apparatus. In this case, the person (or another person carrying out the examination or a helper) can therefore manually measure and then input the distance.

If the user photographs himself in the manner of a so-called selfie for examination, the arm length of the user can also be estimated or input in step 70 (or the length of an aid such as a "selfie stick") and the distance can be estimated on the basis thereof.

The orientation of the mobile computer apparatus, for example an angle relative to the face, can be additionally determined in step 70. Internal position sensors of the computer apparatus, as are usually present in smartphones for example, can be used for this purpose.

In step 71, the illumination is then activated using the component mounted on the housing of the mobile computer apparatus, as described with reference to FIGS. 1-6. The light source 22 of the smartphone 20 is activated for this purpose in the systems in FIG. 2 or 3. Light source elements 41, 50A-50C and 61 of the component, in particular of the enclosure element, are activated in the systems in FIG. 4, 5 or 6. This can also already take place before step 70. It is therefore clear that the sequence illustrated should not be interpreted as restrictive.

In step 73, at least one recording of an image of the person, in particular of the eye(s) of the person, for whom the corrective lens determination is to be carried out, is then carried out. In step 74, the eye refraction is finally determined by means of eccentric photorefraction based on the image recorded in step 73.

In one exemplary embodiment, the pupil of the eye to be examined is first of all detected in the recorded image for this purpose and a pupil diameter for which there is currently no longer any saturation of the brightness in the pupil is defined. The brightness profile is then analyzed, in which case such an analysis can be carried out for a color image (RGB image—red, green, blue) or else separately according to color channels or else for one color channel over the entire pupil diameter. In the simplest case, the visual defect of the eye can be determined from the gradient of this brightness profile, for example based on a previous calibration with eyes having a known visual defect or with optical units which simulate such a visual defect.

Figure 8A:
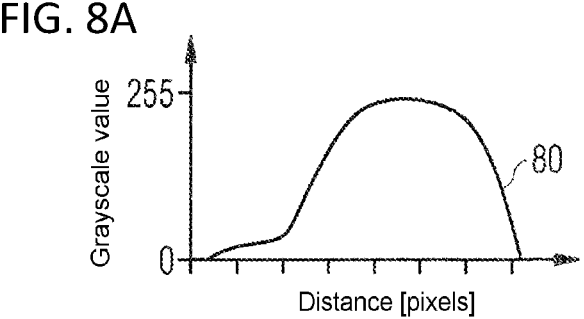
FIGS. 8A-8D show graphs for elucidating the evaluation of an image recording in some exemplary embodiments.
Figure 8B:
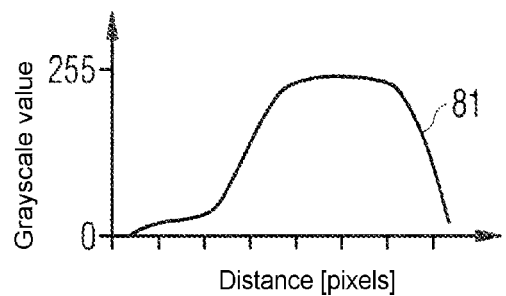
Figure 8C:
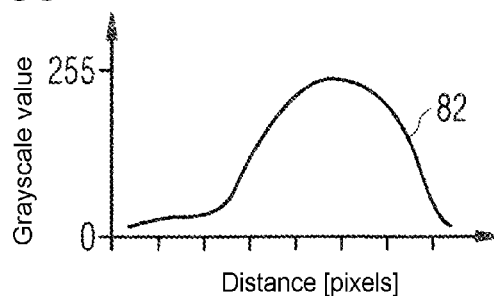
Figure 8D:
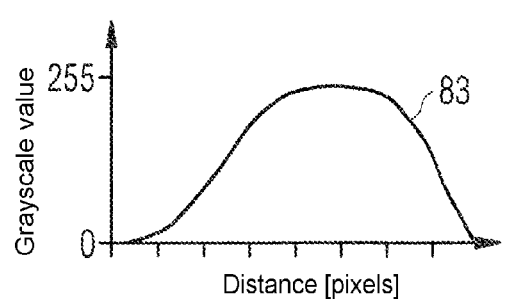

As an example, FIGS. 8A-8D show examples of such brightness profiles. These examples are used only for elucidation and differ, for example, depending on the visual defect of the eye being examined. A curve 80 in FIG. 8A shows a brightness distribution (grayscale value) in a recorded color image of an eye over the diameter of the pupil (in pixels of the image). A curve 81 in FIG. 8B shows the brightness distribution for the red component, a curve 82 in FIG. 8C shows the brightness distribution for the green component and a curve 83 in FIG. 8D shows the brightness distribution for the blue component of the curve 80 from FIG. 8A. In this case, as illustrated in FIGS. 8A-8D, the brightness can be measured along a line over the entire diameter of the pupil, but may also be carried out, for example, within a section of the eye, for example a rectangle. As already explained, the refraction of the eye in the respective meridian being examined (that is to say a meridian which is defined by a line between the light source and the camera) can then be directly inferred from the rise in the brightness in the pupil (that is to say the rise in the curves 80 to 83, for example) using a known conversion factor or known relationships. Only the color channel with the least scattering can also be used for the evaluation, which may be the blue color channel, for example.

Steps 71 and 73 can also be carried out repeatedly in order to record a plurality of images with different illumination directions in order to measure different meridians. For this purpose, different wedges of light sources 41 are activated in succession in step 71 in the system in FIG. 4 in order to thus illuminate the eye to be examined in succession from different directions, or light sources which are arranged in different directions starting from the camera 23 in the system in FIG. 5 are activated in succession. An image of the eye is then recorded in step 73 for each direction, as a result of which a meridian defined by the position of the activated light source and the position of the camera is measured. The eye refraction is then determined in step 74 on the basis of the images recorded in this manner.

Figure 9:
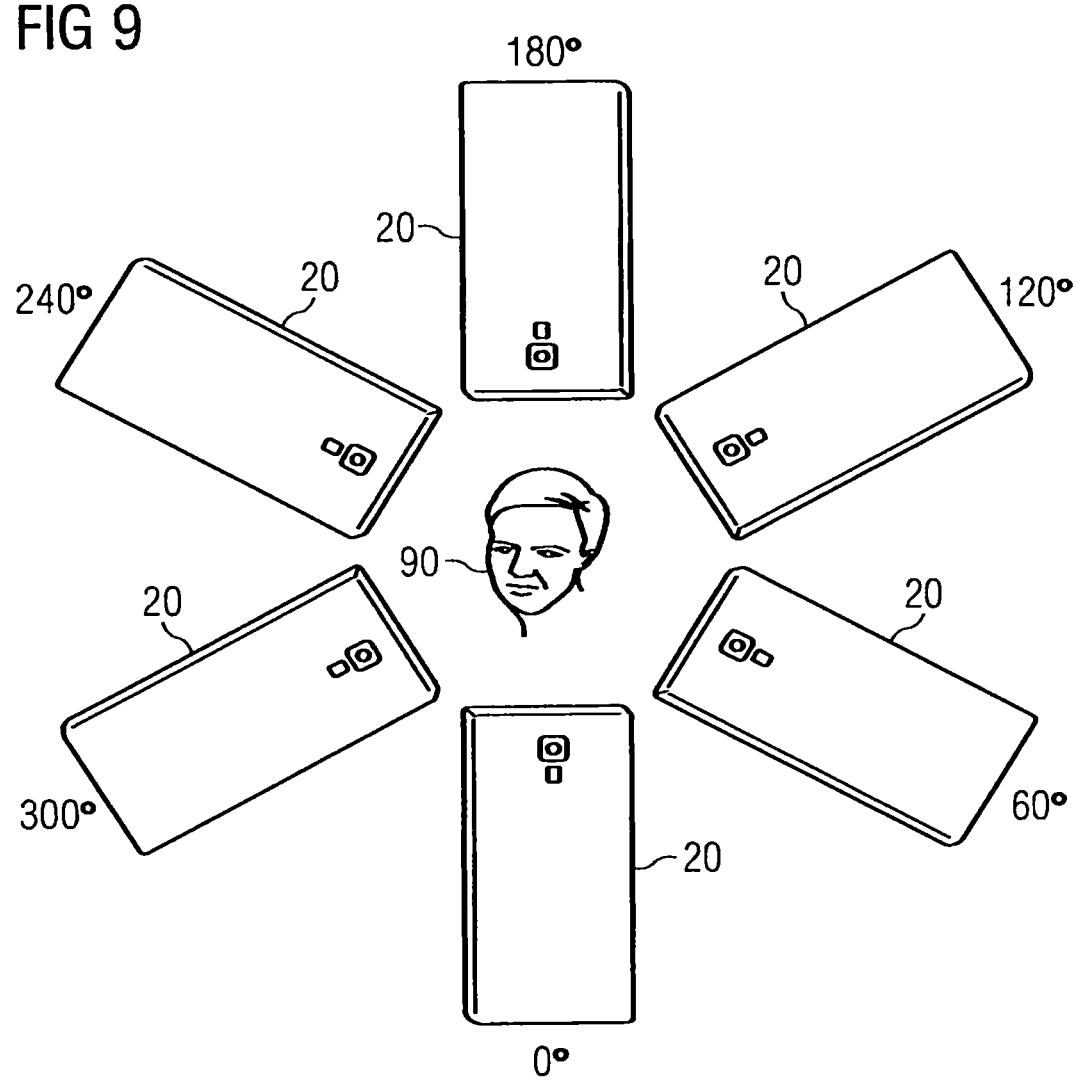
FIG. 9 shows an illustration for elucidating an orientation of a smartphone in accordance with one exemplary embodiment.

For systems, such as the systems in FIGS. 1, 2 and 6, in which one or more light sources are arranged only on one side of the camera 23 of the smartphone 20, the smartphone 20 can be positioned at different angles with respect to the face during recording in order to measure a plurality of meridians, as illustrated in FIG. 9. FIG. 9 shows the smartphone 20 at different angular positions (for example 0°, 60°, 120°, 180°, 240°, 300°) with respect to the face 90. In this case, opposite angular positions (for example 0° and 180°) measure the same meridian and therefore do not provide any additional information. Three angles which are at a distance of 60° from one another (for example 0°, 60°, 180°) provide good coverage of a semicircle (180°) in this case, wherein the other semicircle fundamentally provides the same information, as explained above. In this case, the camera of the smartphone 20 is then facing the face during recording and the optical axis of the camera can have substantially the same position for all recordings. Even if not explicitly illustrated in FIG. 9, the smartphone 20 is then provided with a corresponding optical component (for example as shown in FIGS. 1-6) during recording. In one exemplary embodiment, the illustrated positions of 0°, 60° and 120° are used to determine the sphere, cylinder and axis of an eye to be measured. The other positions of 180°, 240° and 300° can be additionally used to increase the measurement accuracy (for example by means of averaging). In this case, as explained in step 70 in FIG. 7, the angle of the mobile computer apparatus can be determined by means of internal position sensors of the mobile computer apparatus, as are usually present in smartphones or tablet computers, for example.

Such a measurement of a plurality of meridians makes it possible to determine low-order aberrations, usually referred to as sphere, cylinder and axis in eye examination. A plurality of recordings are carried out for this purpose, as explained, in which case the illumination is effected from different directions.

In this case, two assumptions are usually taken as a basis: (1) the axes with the greatest and smallest visual defect are perpendicular to one another and (2) the visual defect changes over the meridians according to the Gaussian theorem corresponding to a sine-squared function. In order to be able to adapt this function to the measured values, measurements in at least three meridians are required. This can conventionally be achieved, for example, by constructing a "three-armed" retinoscope (that is to say a device for corrective lens determination) in which the edges of individual eccentric photorefractors are arranged at the angles of 0°, 60° and 120° (or any other arrangement). In exemplary embodiments according to the invention, measurements of different meridians are carried out by means of illumination from different directions, as explained above.

Such measurements in three meridians are then used to calculate the sphere, cylinder and axis as follows, wherein, in the following formulas, R1 denotes the determined refraction for a measurement with illumination from 0°, R2 denotes the refraction for a measurement with illumination at 60°, and R3 denotes the refraction for a measurement with illumination at 120°, wherein 0° corresponds to illumination of the eye from below. Corresponding equations can be set up for other directions:

$$\text{Sphere} = A + \sqrt{B^2 + D^2}$$

$$\text{Cylinder} = A - \sqrt{B^2 + D^2}$$

$$\text{Axis} = 0.5 * \arctan\left(\frac{D}{B}\right)$$

where $$A = \frac{R1 + R2 + R3}{3}$$

$$B = \frac{2*R1 + R2 + R3}{3}$$

$$D = \frac{R2 - R3}{\sqrt{3}}$$

More detailed information on such calculations is found in the technical literature, for example Schaeffel F, Farkas L, Howland H. "Infrared photoretinoscope", Applied Optics 1987 or Gekeler F, Schaeffel F, Howland H C, Wattam-Bell J. "Measurement of astigmatism by automated infrared photoretinoscopy". Measurement of astigmatism by automated infrared photoretinoscopy. Optom Vis Sci. 1997 July; 74(7):472-82.

Parameters such as the sphere, cylinder and axis or other information relating to the refraction with a compact apparatus can therefore be determined in a cost-effective manner using the illustrated systems comprising a mobile computer apparatus and an optical component. Smartphones, tablet PCs and the like can therefore be equipped with the discussed optical components and a corresponding app in order to be able to measure the eye(s) of a person in an effective manner.

The invention claimed is:

1. A system for corrective lens determination by eccentric photorefraction, the system comprising:
   a mobile computer apparatus including:
      a housing;
      a camera installed in the housing;
      a processor; and
      an associated non-transitory storage memory storing a computer program having a program code which, when executed on the processor, carries out corrective lens determination of an eye of a person to be examined by eccentric photorefraction; and
   an enclosure element configured to completely or partially enclose the mobile computer apparatus and having at least one light source,
   wherein the at least one light source is arranged on an outer side of the enclosure element facing away from the camera, and
   wherein the at least one light source is configured to illuminate an eye with an eccentricity during an eccentric photorefraction measurement.

2. The system as claimed in claim 1, wherein the at least one light source comprises a multiplicity of light sources arranged in a wedge shape.

3. The system as claimed in claim 1, wherein the at least one light source comprises a plurality of light sources arranged at different respective distances from the camera, and wherein the system is configured to set different measurement ranges for the eccentric photorefraction by activating different light sources.

4. The system as claimed in claim 1, wherein the enclosure element comprises an opening for the camera of the mobile computer apparatus, and wherein the at least one light source is arranged adjacent to the opening.

5. The system as claimed in claim 4, wherein the at least one light source comprises a plurality of light sources arranged at different respective distances from the opening.

6. The system as claimed in claim 1, wherein the mobile computer apparatus is configured to control the at least one light source for carrying out the eccentric photorefraction.

7. A method for corrective lens determination, comprising:
   illuminating a person's eye with light;
   recording an image of the person's eye with a camera of a mobile computer apparatus; and
   carrying out an eccentric photorefraction determination based on the recorded image of the person's eye;
   wherein the light from at least one light source of an enclosure element, which is configured to completely or partially enclose the mobile computer apparatus, is emitted with an eccentricity for the eccentric photorefraction, and
   wherein the at least one light source is arranged on an outer side of the enclosure element facing away from the camera.

8. The method as claimed in claim 7, wherein the light is emitted by a multiplicity of light sources of the enclosure element which are arranged in a wedge-shaped manner.

* * * * *